United States Patent [19]
Kleinman

[11] Patent Number: 4,597,094
[45] Date of Patent: Jun. 24, 1986

[54] AUTOMATED SETTING OF TECHNIC FACTORS FOR X-RAY EXAMINATIONS WITH A RANGING TRANSDUCER MOVING IN AND OUT OF THE X-RAY BEAM PATH

[75] Inventor: Bennett Kleinman, Amityville, N.Y.

[73] Assignee: Bennett X-Ray Corp., Copiague, N.Y.

[21] Appl. No.: 557,353

[22] Filed: Dec. 1, 1983

[51] Int. Cl.[4] ............................................. H05G 1/10
[52] U.S. Cl. ..................................... 378/95; 378/116
[58] Field of Search ................. 378/116, 95, 117, 207

[56] References Cited

U.S. PATENT DOCUMENTS

| | | | |
|---|---|---|---|
| 4,027,156 | 5/1977 | Robinet | 378/117 |
| 4,137,460 | 1/1979 | Fitzsimmons | 378/117 |
| 4,403,337 | 9/1983 | Kleinman | 378/95 |

Primary Examiner—Craig E. Church
Attorney, Agent, or Firm—Cooper, Dunham, Griffin & Moran

[57] ABSTRACT

Disclosed is automated setting of x-ray technic factors (e.g., KV, MA and exposure time) on the basis of (a) automated determination of the thickness of the body part to be imaged by a non-contact ranging system, (b) push button selection for the type of examination, and (c) push button selection for the type of body physique. The automatically determined technic factors and/or thickness are displayed to allow for manual override, and other failsafe features are provided as well. For better results, the ranging transducer is in the path of, and aligned with the axis of, the x-ray beam while producing ranging information, but is out of the x-ray beam path for the actual x-ray examination. An interlock is provided so that the x-ray beam is not on when the ranging transducer is in the beam path.

6 Claims, 4 Drawing Figures

AUTOMATED SETTING OF TECHNIC FACTORS FOR X-RAY EXAMINATIONS WITH A RANGING TRANSDUCER MOVING IN AND OUT OF THE X-RAY BEAM PATH

BACKGROUND AND SUMMARY OF THE INVENTION

The invention relates to x-ray machines and specifically to automated setting of technic factors such as exposure time, KV (the operating voltage to be applied to the x-ray tube) and MA (the current in milliamperes to be supplied to the x-ray tube). In at least some x-ray machines it is important to select technic factors which avoid exposing the body to any unneeded radiation and yet produce a picture which is clear enough to be useful for diagnostic purposes. Typically three factors are set for a particular examination: the voltage and current (in KV and MA) which will energize the x-ray tube and the exposure time. The criteria for determining an optimum combination of KV, MA and exposure time include the distance between the focal spot (from which x-rays emanate) and the image receptor plane (e.g., the x-ray film plane), the type of examination or procedure (e.g., an examination of the pelvis, the skull, the stomach, the esophagus, etc.) and the thickness of the patient part which is to be imaged. Standard technic charts are published and used in the industry to find the KV, MA and exposure time for the given type of examination and for a given thickness of the body part to be imaged. In a typical prior art examination the body is positioned against the image receptor or body support, the x-ray technician measures the thickness of the body part to be imaged, using callipers or some other mechanical instrument, looks up the corresponding technic factors on the chart, and sets corresponding KV, MA and exposure time (or only KV and MAS—milliamperes per second) by using controls on a panel. The procedure is time consuming and, of course, prone to human error in that the technician may incorrectly look up or set the necessary technic factors, and the body may meanwhile move and thereby change the thickness of the part which is actually imaged.

In one known prior art system an ionization chamber is positioned adjacent the image plane to detect when the image receptor has received sufficient radiation for a clear image so that the x-ray beam can be turned off at the right time. However, the system is so expensive and requires so much careful calibration that it is believed to be rarely used outside large and sophisticated radiology centers, and it is believed that most users still rely on manually measuring the thickness of the body part to be imaged and manually setting the technic factor controls.

A prior invention by the same applicant, described in U.S. No. Pat. No. 4,403,337, which is hereby incorporated by reference, provided a system in which a non-contact automatic measurement is made of the thickness of the patient part to be imaged. This measurement is automatically used, together with technician-selected type of examination and type of body to be imaged, for automatic setting of an optimum combination of technic factors.

In the example described in detail in U.S. Pat. No. '337, a ranging transducer 20 was shown as mounted at the outside of a collimator box 22 which in turn is mounted on x-ray tube 10. Specifically, while the invention claimed in the U.S. Pat. No. '337 patent is not so limited, the transducer 20 is shown as fixedly mounted to a side wall of collimator box, outside the path of the x-ray beam from x-ray tube 10 to image receptor 16. While that exemplary arrangement is still believed to be operable and useful, it has been discovered since applying for said U.S. Pat. No. '337 patent that it is possible to have the ranging transducer in the path of the x-ray beam while making the ranging measurements but out of said path when the x-ray beam is on for the actual x-ray examination. It was discovered that, unexpectedly, significantly better results are obtained when the ranging measurements are taken when the transducer is in the path of the x-ray beam and, preferably but not necessarily, is aligned with the x-ray beam axis. Preferably, but not necessarily, the transducer movement and the x-ray tube energization circuits are interlocked so that the x-ray beam cannot be turned on while the ranging transducer is in its path—as a safety precaution against irradiating the body being examined with radiation modulated by passing through the ranging transducer structure. The movement of the ranging transducer into and out of the x-ray beam path, and the ranging operation, can be controlled either from the control panel (which typically is in an area shielded from x-ray exposure) or by means of manual controls at the structure to which the x-ray tube is affixed.

In an exemplary embodiment, an x-ray machine includes an x-ray source and an image receptor, such as film in a suitable holder, which has an image plane at a known (or determinable) distance from the source and is irradiated with an x-ray beam therefrom when the source is energized. The body to be x-rayed is positioned against a body support, on a table or against an upright support, such that the distance between the image plane and the body part to be imaged is fixed but the distance between that body part and the source is unknown—as it is determined by the unknown thickness of the body part to be imaged. A transducer fixed with respect to the source sends a ranging signal (e.g., a sonic or a light signal, visible or not) toward the body part to be imaged and receives the reflection of said radiation therefrom. In the example of using a sonic ranging signal a travel time derivation circuit is coupled with the transducer and derives therefrom a signal determined by the two-way travel time of the sonic signal, i.e., the time the sonic signal takes to travel from the transducer to the body part to be x-rayed and back from that body part to the transducer. The two-way travel time signal is converted to a thickness signal defining the thickness of the body part to be imaged with x-rays, and an exposure time derivation circuit derives, in part on the basis of that thickness signal and in part on the basis of technicianselected push buttons for the type of x-ray examination and for the type of body physique, a signal defining the exposure time for imaging said patient part. The type- of-examination and type-of-body-physique push buttons (or other manually operated devices) which are set by the technician automatically determine the KV and MA at which the x-ray source will be operated. The system can periodically recheck the body thickness and, if necessary, update the automatic setting of technic factors, until the technician pushes a button (or operates some other control) to initiate actual x-ray exposure at the so selected technic factors. Failsafe provisions are made against exceeding a maximum permissible exposure time which can be selected by the technician for the particular type of examination and/or body, and maximum permissible MAS (current flow per second to the x-ray tube).

The ranging transducer is mounted to move between an active position, in which it is in the path of the x-ray beam, and preferably but not necessarily aligned with its axis, and an inactive position, in which it clears that x-ray beam. Means can be provided for interlocking the transducer movement with the x-ray tube energization circuit to prevent turning on the x-ray beam while the ranging transducer is in its path.

DETAILED DESCRIPTION OF AN EXEMPLARY EMBODIMENT

Figure 1:
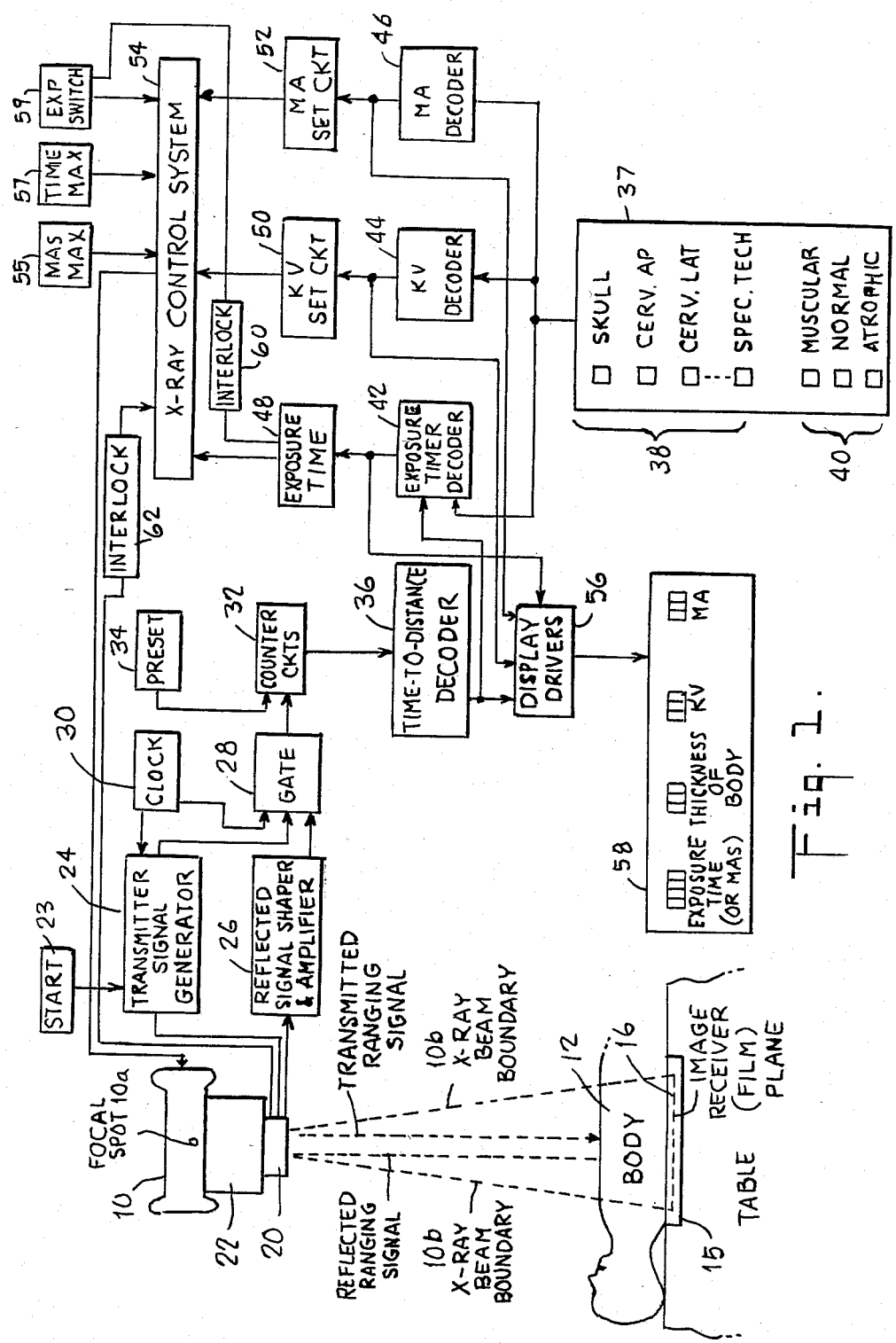
FIG. 1 is a partly schematic and partly functional block diagram illustrating an exemplary embodiment of the invention.

Referring to FIG. 1, an x-ray tube 10 when energized generates at its focal spot 10a, a beam of x-rays whose boundaries are labelled 10b. The x-ray beam, when on, irradiates a body 12 positioned on a table 14. The x-rays which pass through body 12 impinge on an image receptor 15, such as a film holder which has an image (film) plane at 16. For a given examination, the distance between focal spot 10a and image plane 16 is fixed and known (or can be determined). For example, in one type of radiographic examinations the distance is typically either 40 inches or 72 inches. What is not initially known, because it depends on the shape, size and position of the body part to be imaged, is the thickness of tissue through which x-rays must pass in order to reach image receptor 15. Knowing this thickness is important because it must be taken into account in determining the optimum technic factors. The relevant thickness is measured herein with the help of a ranging transducer structure 20 mounted at the underside of a collimator box 22, which in turn is mounted on x-ray tube 10. When energized by transmitted signal generator 24, and assuming it is in the "active" position in the path of (and preferably aligned with the axis of) x-ray beam 10b, transducer 20 sends a ranging signal (e.g., a sonic pulse) toward body 12 and the facing surface of the body reflects it as a reflected ranging signal (e.g., an echo pulse). Upon receipt of the reflected ranging signal, transducer 12 generates an electrical signal supplied to a reflected signal shaper and amplifier 26, which is a part of a travel time circuit 27 also including a gate 28, clock 30, counter circuit 32 and pre-set circuit 34. Clock 30 runs at a high frequency relative to the typical two-way travel times of the ranging signal from transducer 20, e.g., at 550 KHz. Gate 28 opens under the control of a signal from pulse generator 24 at the time transducer 20 sends out the transmitted signal and closes under the control of a signal from shaper and amplifier 26 at the time transducer 20 receives the reflected ranging signal. Accordingly, gate 28 supplies to counter 32 those pulses from clock 30 which occur during the time interval over which the transmitted ranging signal travels from transducer 20 to body 12 and the reflection thereof travels from patient 12 back to transducer 20. Pre-set circuit 34 loads a first portion of counter circuit 32 with a count which corresponds to the two-way travel time between transducer 20 and the surface of table 14, and the pulses supplied to counter circuit 32 from gate 28 are counted up in a second portion of counter circuit 32. The counts in the first and second portions of counter circuit 32 are subtracted therein from each other and the difference signal, which is determined by and thereby defines the thickness of the body part to be imaged at image receptor 15, is supplied to a time-distance decoder 36 which converts it to a thickness signal defining the thickness, e.g. in centimeters, of the body part to be imaged, i.e. that part of body 12 which is between x-ray source 10 and transducer 20 on the one hand and image receptor 15 on the other.

The thickness signal from decoder 36 is supplied to an exposure time decoder 42 which receives an additional input from a control panel 37 having a set of push buttons 38 for selecting the type of examination or procedure to which body 12 is to be subjected and a set of push buttons 40 for indicating the type of body physique. The purpose of decoder 42 is to convert the measurement of body part thickness supplied from decoder 36 and the selections made on control panel 37 into a signal defining the exposure time for the x-ray examination to follow.

The signals from control panel 37 are also supplied to a KV decoder 44 and an MA decoder 46. Decoder 44 provides a signal which defines a particular KV level depending on which button or buttons on control panel 37 are pushed in, and decoder 46 similarly supplies a signal which defines a particular MA level depending on which button or buttons are pushed on control panel 37. The outputs of decoders 42, 44 and 46 are supplied, respectively, to exposure timer 48, KV set circuit 50 and MA set circuit 52, which in turn supply their outputs to x-ray control system 54. Control system 54 controls the supply of power to x-ray tube 10 and, under the control of a technicianoperated switch 59, energizes x-ray tube 10 during an exposure time window determined by timer 48 and at a KV level determined by KV set circuit 50 and with current determined by MA set circuit 52. Failsafe controls are provided in that regardless of its input from timer 48 and circuit 52, control system 54 is prevented from operating the x-ray tube at a level exceeding a maximum permissible MAS (milliamperes per second), set at a circuit 55, e.g. 600 MAS, and is prevented from exceeding a maximum permissible exposure time set manually by the technician at circuit 57 for a given type examination and/or for a given body physique.

As earlier noted, it has been discovered that it is possible to have the ranging transducer in the path of x-ray beam 10b when needed, and that, unexpectedly, significantly better ranging results are produced when the transducer is so positioned. It has been discovered that this is particularly true when there are sharp variations in the thickness of the body part which is within the confines of x-ray beam 10b (which typically is cone-shaped, or pyramid-shaped), for example, when the body part is the foot, or an arm, or a leg. In view of this discovery, the ranging transducer 20 is positioned between the focal spot 10a and the body part to be imaged in the path of x-ray beam 10b and preferably aligned with the beam axis, and is moved out of the x-ray beam path before the x-ray beam is turned on for the actual x-ray examination.

Figure 2:
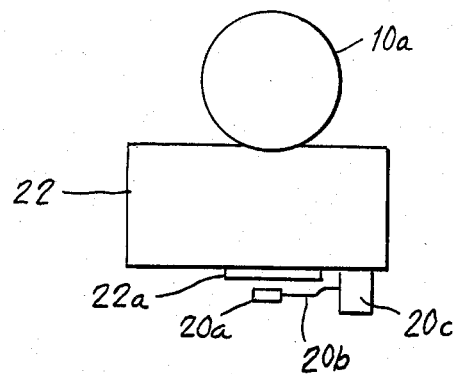
FIG. 2 is a side view of a portion of the embodiment illustrated in FIG. 1, and illustrates in greater detail a ranging transducer structure mounted on the underside of a collimator box which in turn is mounted to the underside of an x-ray tube.
Figure 3:
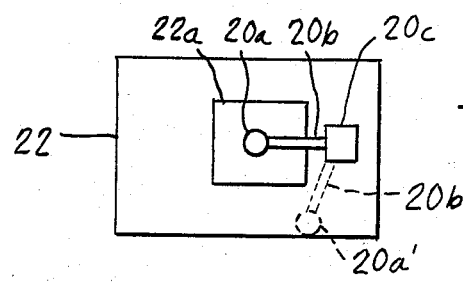
FIG. 3 is a bottom view of the transducer structure and the collimator box illustrated in FIG. 2.

Referring to FIG. 2, the ranging transducer structure comprises a transducer element 20a mounted at the far end of an arm 20b carried by a housing 20c which is secured to the underside of collimator box. Housing 20c encloses an electric motor (not shown) which, as shown in the bottom view of FIG. 3, can move the arm 20b, and with it transducer element 20a, between its active position shown in solid lines at 20a and 20b, and its inactive position shown in dashed lines at 20a' and 20b'. In the active position, transducer element 20a is centered at the center of window 22a of collimator box 22; this window substantially coinsides with the collimated x-ray beam 10b (produced when the x-ray tube is on), and therefore in its active position transducer element 20a is aligned with the beam axis and the ranging signal tends to travel to and come back from the body part to be x-rayed substantially along the x-ray beam axis. For reasons which are not entirely understood, but are believed to include the greater likelihood that a stronger and less noisy reflected ranging signal will return to transducer element 20a along the x-ray beam axis, it has been found that this arrangement is more likely to give a more consistent and accurate indication of the relevant distance.

Figure 4:
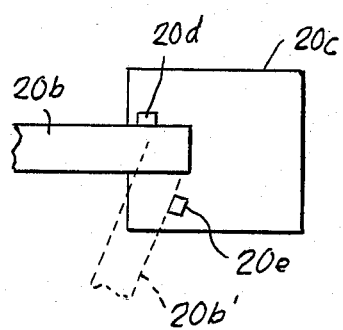
FIG. 4 is an enlarged, partial bottom view of the transducer structure, illustrating the function of limit microswitches.

As it is undesirable to have transducer elements 20a and arm 20b in the path of the x-ray beam during the actual x-raying of the body part being imaged, the motor (not shown) in housing 20c moves arm 20b to the active position only when the x-ray beam is off (e.g., when the x-ray tube is not energized, or if energized, the x-ray beam is cut off by a suitable shutter). For as long as at least one of the arm and transducer element is in the path of the x-ray beam, that beam remains off. It can only come on when the transducer element and the arm are in the inactive position shown in dashed lines. To ensure this, a limit microswitch 20e (see FIG. 4) is activated when the arm reaches the inactive position 20b'. This activation of switch 20e does two things: it turns off the motor (not shown) in housing 20c, so that the arm stops and locks at the inactive position 20b', and it sends a signal to an interlock circuit 62 (see FIG. 1), which in turn releases a suitable lock in x-ray control system 54 to allow it, if activated, to turn on x-ray beam 12b'. Thus, for safety reasons, x-ray control system 54 can turn on the x-ray beam only while the arm carrying the transducer element is in its inactive position 20b'. Another limit microswitch 20d (see FIG. 4) is activated by arm 20b when the arm is at its active position and the transducer element is aligned with the x-ray beam axis (with the x-ray beam being off at the time). Activation of switch 20d stops the motor (not shown) in housing 20c, and stops and locks the arm in its active position shown in solid lines.

In operation, pre-set circuit 34 is manually set to a fixed SID (focal spot to image plane distance), e.g. 40 inches or 72 inches, and is left at that setting for as long as the corresponding relationship between x-ray tube 10 and table 14 is left undisturbed. A particular type of examination is selected by pushing in one of buttons 38, and the type of body physique is accounted for by pushing in one of buttons 40 on control panel 37. The resulting output of control panel 37 is decoded by decoders 44 and 46 and sets the KV level at circuit 50 and the MA level at circuit 52. The outputs of decoders 44 and 46 are additionally supplied to display drivers 56 to energize a 3-digit KV display (or an equivalent meter display) and a 3-digit MA display (or any equivalent meter display) in unit 58 showing the resulting KV and MA selections. The body is then positioned on table 14 (or against a corresponding upright support in case of a stand-up examination), with the body part to be imaged being immediately above (or adjacent) image receptor 15, and a start switch 23 is energized to turn on ranging signal generator 24 and to thereby cause ranging transducer 20 to send out a transmitted ranging signal whose reflection from the body is processed as discussed above to produce a distance signal at the output of decoder 36. If the transducer element 20a is not already in its active position, activation of start switch 23 energizes the motor (not shown) in housing 20c to move arm 20b until it locks against microswitch 20d, in its active position. This thickness signal is supplied to display drivers 56 and is displayed, e.g., in centimeters, at the correspondingly labelled display in unit 58, and is additionally supplied to exposure time decoder 42 to help set exposure timer 48 as discussed above. When the technician is satisfied with the position of the body and, as a precaution, with the exposure time (or MAS), thickness, KV and MA displayed at unit 58, an exposure switch 59 is manually energized. This turns on the motor (not shown) in housing 20c, to move transducer element out of the path of the x-ray beam (which at this time is off), until it is locked against limit microswitch 20e. When switch 20e is so activated, interlock 62 signals x-ray control system 54 to make it energize x-ray tube 10 over the exposure time interval determined by timer 48 and at the KV and MA determined by circuits 50 and 52 respectively. Switch 59 is interlocked with exposure timer 48 through interlock circuit 60 such that the energization of switch 59 has no effect on x-ray control system 54 until after the setting of timer 48 (by an output from decoder 42) has been completed. In addition, failsafe circuits 55 and 57 constrain x-ray control system 54 such that the energization of switch 59 has no effect on x-ray tube 10 if the relationship between the contents of timer 48 and MA circuit 52 is such that the MAS indicated thereby exceeds the maximum MAS set in circuit 55 or if the exposure time set in timer 48 exceeds a maximum exposure time set in circuit 57 by the technician for the given type of examination and/or body physique.

Once a body has been positioned on or against support 14, and for as long as the transducer element remains in its active position (against microswitch 20d), the system can keep rechecking the relevant thickness measurement until it is time to turn on x-ray beam 10b. To implement this signal generator 24 receives an input from clock 30 which enables it to energize transducer 20 a fixed number of times per second, for a corresponding number of updates of thickness measurements. The clock pulses from gate 28 for each new thickness measurements replace the clock pulses previously accumulated in the second part of counter circuits 32 for a previous thickness measurement, and the new thickness measurement updates the thickness display at unit 58 and the contents of exposure timer 48. As noted earlier, if exposure switch 59 is energized while the contents of exposure timer 48 are being updated, x-ray control system 54 waits until the updating of exposure timer 48 is completed before energizing x-ray source 10 on the basis of the contents of exposure timer 48, KV set circuit 50 and MA set circuit 52. Once the transducer element moves away from its active position (away from switch 20d), further changes in the contents of timer 48 and circuits 50 and 52 have no effect on x-ray control system 54 until the x-ray exposure is completed.

In an exemplary implementation, each of decoders 44 and 46 can comprise an EPROM device storing three look-up tables. In a given decoder, each table is for a respective one of the three push buttons 40, and each table stores a respective digital signal for each respective one of push buttons 38. For a given one of decoders 44 and 46 the relationship between the three tables is such that for a given one of the push buttons 38 the signal level for th push button 40 labelled MUSCULAR is 1.4 times that of the signal for the push button 40 labeled NORMAL and the signal stored for the push button 40 labelled ATROPHIC is 0.6 times that stored for the push button labelled NORMAL. For example, referring to MA decoder 46, in the case of the look-up table for the push button 40 labelled NORMAL a signal indicative of 300 milliamperes is stored for the push button 38 labelled SKULL, and a signal indicative of 100 milliamperes is stored for the push button 38 labelled LUMBAR SPINE. In the case of the push button 40 labelled MUSCULAR the corresponding signal for SKULL is 420 milliamperes and for the push button labelled ATROPHIC the same signal is 180 milliamperes. Decoder 42 can similarly comprise an EPROM circuit containing a respective look-up table for each respective one of push buttons 38 and a respective multiplier for each of push buttons 40. Each table stores a respective exposure time value for each of several thickness signals within the range of thickness expected for the respective push button switch 38. The multiplier for the push button 40 labelled MUSCULAR multiplies the exposure time signal derived from the look-up tables for a given thickness and a given push button 38 by 1.4 prior to supplying it to exposure timer 48; the multiplier for push button 40 does the same multiplication by a factor of 1.0; and the multiplier for the push button 40 does the same multiplication by a factor of 0.6. For example, the look-up table for the push button 38 labelled SKULL contains a signal indicative of an exposure time of 1/12th of a second when the thickness signal from decoder 36 indicates 18 centimeters, and contains additional exposure time signals for other thickness signals increasing the exposure time by increments corresponding to 5 MAS per centimeter increase in the thickness dimension. In the case of a chest x-ray selected by a correspondingly labelled push button 38, the respective look-up table in decoder 42 stores an exposure time signal for 1/30th of a second for a chest thickness dimension of 22 centimeters, the exposure time signal increasing by increments corresponding to 1.25 MAS for each centimeter increase in the thickness dimension provided by decoder 36. Of course, the particular values indicated above correspond to a particular selection, and for any given application other relationships between thickness, type of examination, type of body physique, MA and KV can be selected and appropriately stored in the look-up tables and multipliers discussed above. Signal generator 24 can be energized, to initiate a new thickness measurement 3 times per second, but of course this is an arbitrary selection, and a different rate of rechecking can be selected. The output of decoder 42 can be supplied to display drivers 56 and displayed at the correspondingly labelled 4-digit display at unit 58 or, as an alternative, the product of the outputs of decoders 46 and 42, which is the MAS factor for the examination, can be supplied to display drivers 56 and displayed in place of the exposure time in unit 58.

The transmitted ranging signal from transducer 20, in the example of a sonic signal, can be a combination of several cycles at several different frequencies: for example, each transmission can be a pulse which can comprise eight cycles at 60 KHz, eight cycles at 57 KHz, sixteen cycles at 53 KHz and twenty-four cycles at 50 KHz.

As one example the system discussed above for automatically setting technic factors can be incorporated in an x-ray machine of the type available from the Bennett X-Ray Corp. under the designations RD 325, 525 and 625, and it should be clear that for the sake of conciseness the discussion above omits an express description of conventional and well known parts of such an x-ray machine, such as power supply for the x-ray tube, appropriate mechanical supports for the x-ray source and the patient table, etc., and for the same reason omits an express description of the conventional aspects of the circuitry shown in the drawing and discussed above, such as power supplies, details of timing circuitry, etc. It should also be clear that the discussion above relates to a particular exemplary embodiment of the invention but is not limited thereto and that the invention applies to other embodiments and implementations thereof, such as in a fluoroscopic or other type of x-ray machine, and that the scope of the invention is defined only in the appended claims.

As an example of one of the many variations within the scope of the invention as claimed, additional manual switches and associated circuitry can be provided to modify the systems described above such that a special switch is used to control the movement of the transducer element between its active and inactive positions. When so modified, this special switch (which can be at one or both of the control panel and the structure supported near the x-ray tube) can be used to move the ranging transducer to its active position before start switch 23 is energized, and to move the ranging transducer to its inactive position before exposure switch 59 is energized. In this example, switches 23 and 59 are decoupled from the motor driving the transducer element between its two end positions.

I claim:

1. An x-ray machine comprising:
   an image receptor, a support for locating a body at a known distance from the receptor, and an x-ray source which, when energized, produces an x-ray beam which irradiates the receptor after passing through the body;
   a ranging transducer and means for moving the transducer between an active position, in which it is in the path of said x-ray beam and is aligned with the axis thereof, and an inactive position in which it is outside the path of said x-ray beam;
   means for energizing the transducer, when it is in its active position, to cause it to send a ranging signal toward the body and receive the reflection thereof from the body, and for utilizing the operation of the transducer for automatic setting of selected technic factors of said x-ray machine; and
   means for interlocking the x-ray source and the means for moving the transducer to prevent irradiation of the body and receptor with said x-rays when the transducer is in the path of the x-ray beam.

2. An x-ray machine as in claim 1 in which the ranging transducer is between the x-ray source and the image receptor, and moves between its active and inactive positions along a path transverse to the x-ray beam axis.

3. An x-ray machine as in claim 2 including a collimator box secured to the x-ray source to collimate said x-ray beam, and in which the means for moving the ranging transducer comprise a housing secured to the collimator box, an arm extending from the housing and pivoting about an axis in the housing and carrying the ranging transducer at its free end to move it between its active and inactive positions.

4. An x-ray machine as in claim 1 in which the ranging signal sent by the transducer toward the body is a sonic signal.

5. A method comprising providing an image receptor and an X-ray source which, when energized, directs a beam of x-ray toward the receptor, placing a body adjacent the receptor and facing the source, moving a ranging transducer to an active position in which it is in the path of the x-ray beam and is aligned with the axis thereof while the x-ray source is not energized, operating the ranging transducer, when it is in its active position, to send a ranging signal toward the body and receive the reflection thereof from the body, utilizing the operation of the ranging transducer for automatic setting of selected technic factors of the x-ray source, moving the ranging transducer to an inactive position, in which it is outside the x-ray beam, energizing the x-ray source in accordance with the automatically set technic factors, and providing an interlock between the x-ray source and the ranging transducer to prevent irradiation of the body and receptor with said x-ray beam when the transducer is in the path of the x-ray beam.

6. An x-ray machine comprising an image receptor, a support for locating a body to be x-rayed, and an x-ray source which, when energized, produces an x-ray beam which irradiates the receptor after passing through the body, and means for automatically setting technic factors depending on the thickness of the body to be x-rayed comprising a ranging transducer which moves between an active position in which it is in the path of and coaxial with the imaging beam of x-rays and an inactive position in which it is out of said beam and generates, when in its active position, signals indicative of the thickness of the body part to be imaged and means for preventing x raying the body while the transducer is in its active position.

* * * * *